United States Patent [19]

Lin et al.

[11] 4,273,867

[45] Jun. 16, 1981

[54] METHOD AND REAGENT FOR COUNTERACTING LIPEMIC INTERFERENCE

[75] Inventors: Wayne H. T. Lin, Chesterfield; James J. Grib; Larry D. Mosier, both of St. Louis, all of Mo.

[73] Assignee: Mallinckrodt, Inc., St. Louis, Mo.

[21] Appl. No.: 27,388

[22] Filed: Apr. 5, 1979

[51] Int. Cl.³ .................... G01N 33/54; G01N 31/00; G01N 33/48
[52] U.S. Cl. .......................................... 435/7; 435/17; 435/21; 23/230 B; 23/230.3; 23/915; 23/920; 424/1.5; 424/12; 252/408
[58] Field of Search .................. 23/230 B, 915, 230.3, 23/920; 424/2, 12, 1.5, 1; 435/4, 7, 11, 17; 252/408 R; 210/31

[56] References Cited

U.S. PATENT DOCUMENTS

| | | | |
|---|---|---|---|
| 3,899,298 | 8/1975 | Szczesniak | 23/230 B |
| 3,954,409 | 5/1976 | Hsia | 23/230 B |
| 4,028,465 | 6/1977 | Lewin et al. | 424/1 |
| 4,056,468 | 11/1977 | Breiter et al. | 252/408 R |
| 4,111,657 | 9/1978 | Denney et al. | 23/230 B |
| 4,121,975 | 10/1978 | Ullman et al. | 435/7 |
| 4,139,604 | 2/1979 | Gutcho et al. | 23/230 B |
| 4,148,869 | 4/1979 | Deaton | 424/1 |
| 4,166,104 | 8/1979 | Wagner et al. | 23/230 B |

OTHER PUBLICATIONS

Remes, et al., "Radio Immuno Assay-Improvement of the Double-Antibody Separation Method Using Polyethylene glycol in the Media," *Radiochem, Radio Anal. Letters,* vol.34, (1978), pp. 253–260.

Blank-Liss, et al., "A Rapid Radio Immuno Assay for Human α-Fetoprotein", *Clin. Chem. Acta,* vol. 86, (1978), pp. 67–72.

Ritchie, et al., *Automated Immuno Analysis* (Part I) (1978) pp. 90, 102.

Parmelee, et al., "The Presence of Fatty Acids in Human α-Fetoprotein", *J. Biol. Chem.,* vol. 252, No. 7 (1978) pp. 2114–2119.

Hindriks, et al., "Pitfalls of Use of Lipemic Serum with the Technicen SMAC and Dupont ACA", *Clin. Chem.* vol. 24, No. 11 (1978) pp. 2062–2063.

*Primary Examiner*—Thomas G. Wiseman
*Attorney, Agent, or Firm*—Bernard & Brown

[57] ABSTRACT

A method and reagent for counteracting lipemic interference in an assay of a lipid-containing sample, e.g. blood. The method includes the steps of: (a) mixing with the sample prior to or during said assay a high surface area, finely-divided adsorbent having an affinity for lipids, and a nonionic, water-soluble polymer, and (b) precipitating adsorbed lipids in said sample. The reagent includes a high surface area finely-divided adsorbent, and a nonionic, water-soluble polymer having a molecular weight of from about 1,000 to 100,000.

15 Claims, No Drawings

METHOD AND REAGENT FOR COUNTERACTING LIPEMIC INTERFERENCE

This invention relates to a method and reagent for counteracting lipemic interference in an assay of a lipid-containing sample, e.g. blood.

It has been found that lipemia of serum caused by increased concentrations of lipids may disturb, or even make impossible, the assaying of such samples using various assay techniques including, for instance, radio-immunoassay, and enzymatic analysis, especially at short wavelengths. For the diagnosis of, e.g., liver disease, myocardial infarct or other body condition which is often accompanied by hyperlipemia, the accuracy of these measurements can be adversely affected by the presence of lipids in the sample. *Clinical Chemistry*, Vol. 24, No. 11, 1978, pp. 2062-3. Also, in various radioimmunoassay (RIA) techniques, the presence of increased concentrations of lipids in the sample can interfere with the assay. Typically, this interference may be demonstrated in RIA systems by the presence of either a floating precipitate or a flocculation or both in the supernatant of the reaction medium during separation of antibody-bound from unbound antigen. Such interference tends to greatly diminish the accuracy and reproducibility of results in quantitative RIA techniques. The present invention is thus concerned with providing a method for either eliminating or minimizing such interference caused by the presence of lipids, and especially high levels of such lipids, in a sample to be assayed.

Accordingly, the present invention relates to a method for counteracting lipemic interference in an assay of a lipid-containing sample, which comprises: (a) mixing with the sample prior to or during said assay a high surface area, finely-divided adsorbent having an affinity for lipids in a minor amount sufficient to adsorb lipids present in the sample, and a nonionic, water-soluble polymer having a molecular weight of about 1,000 to 100,000 in a minor amount sufficient to accelerate precipitation of lipids in said sample, and (b) precipitating adsorbed lipids in said sample. Mixing of the adsorbent and polymer may be accomplished by various means so long as thorough mixing with the sample is accomplished. Precipitation of adsorbed lipids may also be by various known means although centrifuging is preferred. After precipitation of adsorbed lipids, the precipitate may, if desired, be separated from the supernatant where, for instance, the adsorbent is added prior to the assay, although actual separation is not necessary, for instance, where adsorbent is added during the actual assay.

The present invention also relates to a reagent useful for counteracting lipemic interference in an assay of a lipid-containing sample. The reagent contains a high surface area, finely-divided adsorbent having a high affinity for lipids in a minor amount sufficient to adsorb interfering lipids, and a nonionic, water-soluble polymer having a molecular weight of from about 1,000 to 100,000 in a minor amount sufficient to accelerate precipitation of adsorbed lipids present in the sample. The reagent may be prepared, for instance, by ultrasonic mixing of a polymer-adsorbent suspension in an aqueous solution having a pH of about 4 to 10.

As used herein, the term lipid refers to any one or more of a group of substances that in general are soluble in ether, chloroform, or other solvents for fats but are only sparingly soluble in water, that with proteins and carbohydrates constitute the principal structural components of cells, and that are considered to include fats, waxes, phosphatides, cerebrosides, and related and derived compounds and may even include steroids and carotenoids. In general, according to the invention, the lipid interference of a lipid-containing sample may be reduced at least to a sufficiently low level so that an assay can be performed on the sample without substantial interference from lipids.

Although the sample may be any lipid-containing biological fluid to be assayed, typically it may be whole blood or a blood fraction such as blood serum or blood plasma, all of which may contain lipids in sufficient quantity to interfere with an assay to be performed on the sample. Also, urine may be conveniently treated using the method of the present invention, and assays subsequently performed on the urine sample may be improved.

The adsorbent used in the present invention may be the various high surface area, particulate adsorbents having a high affinity to lipids. These materials are finely divided and generally the particle size is sufficiently small for the solids to become suspended in the sample to an extent that precipitation of solids from the suspension would occur at an unduly slow rate, if to any material extent, in a reasonable time period. Typically, the major portion of such particulate adsorbents may have a particle size of less than about 50 microns, preferably less than about 20 microns, say about 15 nanometers or smaller. The adsorbents may be characterized by a total surface area of at least about 50 square meters per gram, preferably about 100 to 400 square meters per gram, for instance about 300 square meters per gram. Such adsorbents include charcoal, silica gel, talc, bentonite, clay base materials, alumina base materials, magnesia base materials, and cellulose base materials, although silica gel and talc are preferred. Talc is finely powdered, hydrous magnesium silicate. Silica gel is colloidal silica, made by coagulation of hydrated silica, resembling coarse white sand in appearance. The adsorbent may be mixed with the lipid-containing sample in a minor amount sufficient to adsorb a substantial amount of the lipids present in the sample, although the amount may vary depending upon the concentration of lipids in the sample to be removed. In general, less than about 40, preferably about 0.5 to 20, milligrams of adsorbent per milliliter of sample may be provided in the sample.

The nonionic, water-soluble polymer of the invention may have a molecular weight of about 1,000 to 100,000, preferably about 3,000 to 8,000, and it may be mixed with the lipid-containing sample in a minor amount sufficient to accelerate precipitation of adsorbed lipids in the sample, e.g. less than about 100 mg., about 5 to 80 mg., per ml. of sample. Examples of such polymers include polyethylene glycols and Dextrans, as well as other nonionic, water-soluble polymers. Frequently, the polymers may contain two or more hydroxyl groups and can be termed polyhydroxy-containing polymers. Polyethylene glycols and Dextran are preferred. Dextran is a polysaccharide produced by bacteria growing on a sucrose substrate composed of $\alpha$-D-glucopyranosyl units. A preferred Dextran is Dextran-70 which has a molecular weight of about 70,000. A preferred polyethylene glycol is PEG-6000 having a molecular weight of about 6,000-7,500.

The method of the present invention finds application in those radioimmunoassay techniques involving a lipid-containing sample where the separation of antibody-bound antigen from unbound antigen is desired. The method finds particular application to the recently-discovered separation technique which employs a nonionic, water-soluble polymer, such as polyethylene glycol as a precipitating agent for separating the antibody-bound from unbound antigens in RIA techniques. The method of the present invention, for instance, may be applied to the so-called double antibody RIA technique where a serum sample which contains lipids is reacted with a first antibody specific to an antigen in the serum in a reaction medium having a radiolabeled antigen in a known amount, after which a second antibody which is not specific to the antigen, but which is specific to the first antibody, is added to the medium resulting in a mutual agglomeration of the first antibodies bound to antigen and second antibodies to provide a product of sufficient molecular size to be capable of separation by centrifugation. The use of an adsorbent for lipids eliminates the interference caused by lipids during separation of bound and free antigens.

In an embodiment of the present invention, a lipid-containing serum sample to be assayed treated by a method which includes the steps of (a) mixing with the sample prior to the assay or even during the assay a high surface area, finely-divided adsorbent having an affinity for lipids in an amount sufficient to adsorb lipids present in the sample, and a nonionic, water-soluble polymer having a molecular weight of about 1,000 to 100,000 in an amount sufficient to accelerate precipitation of adsorbed lipids in said sample, and (b) precipitating adsorbed lipids in said sample. The adsorbent and polymer may be mixed as a single reagent or as separate reagents, in which event the polymer can be added first. Whether the single reagent embodiment or double reagent embodiment is employed, the adsorbent and polymer are preferably diluted for the reagent(s) in an aqueous buffer to a sufficient extent to facilitate mixing with the sample, e.g. to a concentration of about 0.01% to 5%, preferably 0.05% to 2% by weight of adsorbent and 1% to 15%, preferably 3% to 10% by weight of polymer.

The serum sample which contains lipids may be tested by radioimmunoassay for the presence of prostatic acid phosphatase wherein separation of antibody-bound antigen from unbound antigen is accomplished by the double-antibody technique. A nonionic, water-soluble polymer, and an adsorbent are provided in a reaction medium, and an immunoprecipitation reaction between a first water-soluble anitbody bound to antigen and a second water-soluble antibody which is not specific to the antigen but is specific to the first antibody is accelerated. An example of the latter technique for accelerating such immunoprecipitation wherein polyethylene glycol is provided as the polymer is disclosed in a copending application assigned to the same assignee of the present application (Ser. No. 027,387 filed Apr. 5, 1979), incorporated herein by reference. The accuracy of an assay performed on the lipid-containing sample may be advantageously facilitated and the presence of a floating precipitate or a flocculation in the supernatant or both may be avoided or substantially minimized.

In another embodiment, a similar technique is applied to lipemic serum to be tested for creatine phosphokinase by substantially the same double antibody RIA technique described above in connection with prostatic acid phosphatase.

It has also been found that lipid-containing samples, such as blood serum, can interfere with chemical analyses of sample components, for instance photometric measures of enzyme activities at short wavelengths, and in an embodiment of the present invention, the method is used to treat a sample to eliminate or reduce lipemic interference in such chemical analyses.

In the method of the present invention, the high surface area, particulate adsorbent having an affinity for lipids and the nonionic, water-soluble polymer may be provided for mixing with a sample to be assayed as a single reagent or as separate reagents. When a single reagent is provided, the adsorbent and polymer may be preferably suspended in an aqueous medium that may be buffered at a pH of about 4 to 10. The adsorbent is provided in a minor amount sufficient to adsorb interfering lipids in a sample, e.g. about 0.01% to 5% by weight, preferably about 0.05% to 2% by weight, and the polymer being provided in a minor amount sufficient to accelerate precipitation of adsorbed lipids present in the sample, e.g. about 1% to 15% by weight, preferably about 3% to 10%. These amounts of adsorbent and polymer are based on their total amount. Where the adsorbent and polymer components are provided for mixing with a sample as separate reagents, typically the active ingredient in each, e.g., adsorbent and polymer, respectively, may be preferably suspended in an aqueous medium that may be similarly buffered to a pH described above with respect to the single reagent embodiment. Amounts in the ranges noted above with respect to the active ingredients may be provided in each reagent as can be employed in the single regent. Where separate reagents are provided, it is preferred that the polymer-containing reagent be added to the sample prior to addition of the adsorbent-containing reagent.

Examples of buffers which may be used in the above single reagent, adsorbent-containing reagent and polymer-containing reagent include Tris, a commercially-available, aqueous solution containing tris (hydroxymethyl) aminomethane, Barbitol, a commercially-available, aqueous solution of 5,5-diethyl barbituric acid, and other well-known buffers.

The following example will further illustrate the invention applied in creatine phosphokinase-MB (CPK-MB) radioimmunoassay although it will be appreciated that the invention is not limited to this specific example.

Lipemic serum samples from four patients (A,B,C & D) are provided for testing, in two series of quantitative tests for creatine phosphokinase-MB (CPK-MB). The normal level of CPK-MB in human serum is 0–10 IU/l. In one series, CPK-MB is determined with treatment according to the invention during the assay with silica gel, an adsorbent having affinity for lipids. In another series, also detailed below, silica is omitted.

In the first series in each of four tubes, a radioimmunoassay reaction medium was prepared containing 0.2 ml. lipemic human serum (separate samples A,B,C and D in each tube). Each tube also contained 0.1 ml. first antibody reagent (goat anti-CPK-BB) and 0.1 milliliter I-125 labeled CPK-BB solution. After incubation, to each tube was added a second antibody reagent containing 8.4% polyethylene glycol having a molecular weight of about 6,000, a one to 350 dilution of a secondary antiserum (rabbit anti-goat gamma globulin) 0.1% Triton X-100, 0.1% $NaN_3$ and 1 mg./ml. QUSO G32 Silica (a silica gel commercially available from Philadelphia Quartz Co.). After mixing, each of the tubes was subjected to centrifugation without any incubation. The supernatant (free antigen) was decanted and the precipitate containing antigen-antibody complex was measured for radioactivity. The results are set forth below in the Table.

In the second series, the same procedure set forth above was followed except that silica was eliminated from the reaction medium. The results are set forth below in the Table.

TABLE

| Lipemic Patient Sample | CPK-MB Determination without silica gel | CPK-MB Determination with silica gel |
|---|---|---|
| A | 74 IU/l | 5.0 IU/l |
| B | >250 IU/l | 3.7 IU/l |
| C | >250 IU/l | 6.3 IU/l |
| D | 26 IU/l | 10.0 IU/l |

As illustrated in column 2 in the Table, the determination of CPK-MB based upon measurements of radioactivity for the samples were greatly distorted due to lipemic interference caused by the presence of lipids in the serum samples. This interference was substantially eliminated by the presence of adsorbent for lipids as illustrated by the results set forth in column 3.

What is claimed is:

1. In a double antibody immunoassay for a substance in a lipid-containing sample, wherein the improvement comprises (a) mixing with the sample a finely-divided adsorbent selected from the group consisting of charcoal, silica gel, talc, bentonote, clay base materials, aluminia base materials, magnesia base materials, and cellulose base materials having a surface area of at least 50 square meters per gram and having an affinity for lipids in an amount sufficient to adsorb lipids present in said sample, and a nonionic, water-soluble polhydroxypolymer having a molecular weight of about 1,000 to 100,000 in an amount sufficient to accelerate precipitation of adsorbed lipids in said sample, (b) precipitating said adsorbent containing adsorbed lipids in said sample and (c) measuring said sample for said substance.

2. The assay of claim 1 wherein said sample is selected from blood serum or blood plasma.

3. The assay of claim 1 wherein said adsorbent has an average particle size of less than about 50 microns.

4. The assay of claim 1 wherein said adsorbent and said polymer are added to said sample simultaneously in a lipid-adsorbing reagent containing said adsorbent and said polymer and an aqueous solution having a pH of about 4 to 10.

5. The assay of claim 4 wherein said lipid-adsorbing reagent is prepared by ultrasonic mixing of said adsorbent and said polymer in said aqueous solution.

6. The assay of claim 1 wherein said adsorbent and said polymer are added to said sample as separate reagents, an adsorbent-containing reagent and a polymer-containing reagent, wherein the adsorbent and polymer is each present in its said reagent and said reagents further include an aqueous solution having a pH of about 4 to 10.

7. The assay of claim 1 wherein the amount of said adsorbent is less than about 40 milligrams of adsorbent per milliliter of sample and the amount of said polymer is less than about 100 milligrams of polymer per milliliter of sample.

8. The assay of claim 1 wherein said assay is radioimmunoassay and said substance is prostatic phosphatase.

9. The assay of claim 1 wherein said assay is a radioimmunoassay and said substance is creatine phosphokinase.

10. The assay of claim 1 wherein said measuring is a photometric measurement of enzyme activity.

11. The assay of claim 1 wherein said polymer is polyethylene glycol.

12. The assay of claim 1 wherein the substance to be assayed is an antigen.

13. A reagent useful for counteracting lipemic interference in double antibody immunoassay of a lipid-containing sample, which comprises: a finely-divided adsorbent having a surface area of at least 50 square meters per gram and having a high affinity for lipids in an amount sufficient to adsorb lipids; and polyethylene glycol having a molecular weight of about 1,000 to 100,000 in an amount sufficient to accelerate precipitation of adsorbed lipids in said sample.

14. The reagent of claim 13 wherein said adsorbent is one having an average particle size of less than about 20 microns and is selected from silica gel and talc.

15. The reagent of claim 13 wherein said adsorbent and said polyethylene glycol are in an aqueous solution having a buffered ph of about 4 to 10.

* * * * *